United States Patent [19]
DeLuca et al.

[11] Patent Number: 6,022,555
[45] Date of Patent: Feb. 8, 2000

[54] ANIMAL FEED CONTAINING CARBOXYLIC ACIDS

[75] Inventors: Hector F. DeLuca, Deerfield, Wis.; David H. Baker, Champaign, Ill.

[73] Assignee: Wisconsin Alumni Research Foundation, Madison, Wis.

[21] Appl. No.: 08/924,607

[22] Filed: Sep. 5, 1997

[51] Int. Cl.$^7$ .................................................. A61K 31/19
[52] U.S. Cl. ...................... 424/442; 424/489; 424/195.1; 514/167; 514/557; 426/807
[58] Field of Search ..................... 424/438, 442, 424/489, 195.1, 600, 601–603, 606, 677, 719, 722; 514/167, 553, 552; 426/635, 807

[56] References Cited

U.S. PATENT DOCUMENTS

| | | | |
|---|---|---|---|
| 4,952,415 | 8/1990 | Winowiski et al. | 426/285 |
| 5,154,925 | 10/1992 | Edwards, Jr. | 424/422 |
| 5,316,770 | 5/1994 | Edwards, Jr. | 424/442 |
| 5,366,736 | 11/1994 | Edwards, Jr. | 426/2 |
| 5,516,525 | 5/1996 | Edwards, Jr. | 424/442 |

FOREIGN PATENT DOCUMENTS

| | | |
|---|---|---|
| 0004691 | 10/1979 | European Pat. Off. . |
| 0383116 | 8/1990 | European Pat. Off. . |
| 2083997 | 4/1982 | United Kingdom . |
| WO92/20240 | 11/1992 | WIPO . |
| WO9319759 | 10/1993 | WIPO . |
| WO96/24258 | 8/1996 | WIPO . |

OTHER PUBLICATIONS

XP–002082997, Hohler et al, "Effekt einer abgestuften Zn–Zufuhr und Zulagen von Citronensaure zu einer Mais–Soja–Diat auf Leistungsparameter und Mineralstoffverwertung beim Ferkel", Journal of Animal Physiology and Animal Nutrition, vol. 71, No. 4/5, 1994, pp. 189–199, 1994.
Abstract XP–002082998, Hohler, "Influence of Supplementing a Maize–Soybean Meal Diet with Citric and Fumaric Acid on the Utilization of Zinc and Other Minerals in Piglets", Derwent Publications, Ltd., London, GB, Mar. 23, 1994.
Abstract XP–002082999, Anderson, Increasing Mineral Bio–Availability in Humans or Animal Digestive System Esp. of Ruminants—Comprises Using Edible Mixt. Composed of Di– or Trivalent (on source and edible foodstuff); Derwent Publlications, Ltd., London, GB, Mar. 23, 1994.
"Phytase Supplementation and Waste Management", Proc. BASF Technical Symp. at Arkansas Nutr. Conf., pp. 21–44, 1994.
Devereux et al, "Animal Feeds: Phosphate Supplements", Chemical Economics Handbook–SRI International, 1994.

Mitchell et al, "Effects of Phytase and 1,25–Dihydroxycholecalciferol on Phytate Application and the Quantitative Requirement for Calcium and Phosphorus in Young Broiler Chickens", 1996 Poultry Science 75:95–110.
Erling Tvedegaard, "Absorption of Calcium, Magnesium and Phosphate During Chronic Renal Failure and the Effect of Vitamin D in Rabbits," Zeitschrift Für Versuchstierkunde, vol. 27, No. 3/4, pp. 163–168, 1985.
Robert R. Biehl et al, "1α–Hydroxylated Cholecalciferol Compounds Act Additively with Microbial Phytase to Improve Phosphorus, Zinc and Manganese Utilization in Chicks Fed Soy–based Diets," Journal of Nutrition, vol. 125, No. 9, pp. 2407–2419, 1995.
Kevin D. Roberson et al, "Effects Of 1,25–Dihydroxycholecalciferol and Phytase on Zinc Utilization in Broiler Chicks," Poultry Science, vol. 73, No. 8, pp. 1312–1326, 1994.
R.H. Harms et al, "Some Observations on the Influence of Vitamin D Metabolites when Added to the Diet of Commercial Laying Hens," Poultry Science, vol. 69, No. 3, pp. 426–432, 1990.
K. Hove et al, "Prevention Of Parturient Hypocalcemia: Effect of a Single Oral Dose of 1,25–Dihydroxyvitamin $D_3$," Journal of Dairy Science, vol. 65, No. 10, pp. 1934–1940, 1982.
Seiji Aoyagi et al, "Effect of microbial phytase and 1,25–dihydroxycholecalciferol on dietary copper utilization in chicks," Poulty Science, vol. 74, No. 1, pp. 121–126, 1995.
Pileggi et al, "The Role of Vitamin D and Intestinal Phytase in the Prevention of Rickets in Rats on Cereal Diets", Department of Biochemistry, College of Agriculture, University of Wisconsin, Madison, Wisconsin, pp. 194–204, Jan. 21, 1955.
Pileggi et al, "Citrate in the Prevention of Rickets in Rats", Department of Biochemistry, College of Agriculture, University of Wisconsin, Madison, Wisconsin, pp. 52–57, May 9, 1955.

*Primary Examiner*—Neil S. Levy
*Attorney, Agent, or Firm*—Andrus, Sceales, Starke & Sawall

[57] ABSTRACT

An animal feed containing a carboxylic acid either as the sole active ingredient or in combination with 1α-hydroxylated vitamin D compounds and/or phytase. The carboxylic acid or the combination of carboxylic acid with vitamin D compounds and/or phytase causes improved utilization of phosphorus, calcium, potassium, magnesium, zinc, iron and manganese in animal feed so as to minimize, or perhaps eliminate, the need for supplemental quantities of these minerals in an animal diet. In addition, low phosphorus containing animal feeds reduce the polluting effects on the environment since less phosphorus is excreted in the animal's feces which are then spread on agricultural land.

64 Claims, No Drawings

ANIMAL FEED CONTAINING CARBOXYLIC ACIDS

STATEMENT REGARDING FEDERALLY SPONSORED RESEARCH OR DEVELOPMENT

This invention was made with United States government support awarded by the following agencies:

NIH Grant No. DK14881

The United States has certain rights in this invention.

BACKGROUND AND SUMMARY OF THE INVENTION

The present invention relates to an animal feed containing carboxylic acids either as the sole active ingredient or in combination with a bioactive 1α-hydroxy vitamin D compound and/or the enzyme phytase. The use of these carboxylic acids, preferably citric acid, in animal feeds removes calcium from plant based phytate complexes thereby allowing the phytate to solubilize making the phosphorus contained therein bioavailable for animals. These carboxylic acids also increase utilization of the phosphorus available from inorganic sources in the diet. This results in a feed composition having a severe reduction of, and possibly the complete elimination of, supplemental inorganic phosphorus as an ingredient.

Up to 80% of the phosphorus (P) present in plant foods and feeds exists as a complex of phytic acid (myoinositol hexaphosphate), hereinafter referred to as phytate. Phytate may structurally be illustrated by the following formula:

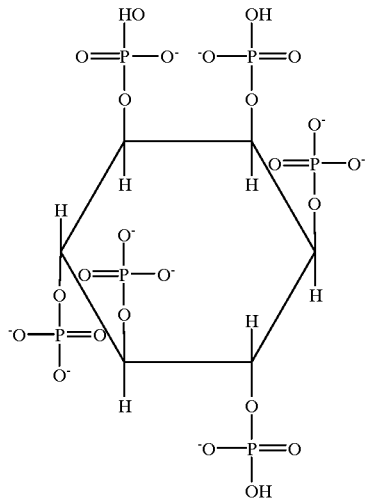

The P in phytate cannot be totally digested by simple-stomached animals, including humans, and it therefore passes through the gastrointestinal (GI) tract and is excreted in the feces. In animal nutrition, this is accounted for in diet formulation whereby 1.5 to 2.0% of an inorganic phosphate source is supplemented to meet the animal's minimal P requirement. Addition of inorganic P to poultry, swine, companion animal, and fish diets is expensive. It is often stated that supplemental P for these species is the third most expensive dietary ingredient, after energy and protein. The body requires P for formation of bones and teeth, for phospholipid (cell membrane structure) and nucleic acid (RNA, DNA) synthesis, for synthesis of ATP and other high-energy P compounds, and for proper acid-base balance in the body. Roughly 85% of I.the body P is in the skeleton. Bone is comprised of 50% organic matrix (protein in the form of collagen, and lipid) and 50% inorganic material (mostly a Ca-P salt. i.e., hydroxyapatite).

Supplemental inorganic P is provided to animal diets in one of three feedgrade forms; dicalcium phosphate (18.5% P), monocalcium phosphate (21.5% P) or deflorinated phosphate (18.0% P). The combined total market for these products is estimated to be 675 million dollars per year in the U.S., Canada, Mexico, Western Europe and Japan. If one were to include South America, Eastern Europe, Asia, Africa, China, India, and Southeast Asia, (where market data are difficult to obtain), the total market for feed-grade phosphates could easily be expected to exceed 1 billion dollars annually. In North America, 50% of feed-grade phosphate consumed is used for poultry feeding. It has been discovered that use of a carboxylic acid as an ingredient in animal feed would severely reduce the need for supplemental inorganic P in animal feed, and if combined with a bioactive 1α-hydroxy vitamin D compound and/or the enzyme phytase, could completely eliminate the need for supplement inorganic P in animal feeds.

Phytate complexes in plant foods and feeds (eg., cereal grains and by-products, beans) also bind cations such as calcium, potassium, magnesium, zinc, iron and manganese (Erdman, 1979) illustrated schematically as follows:

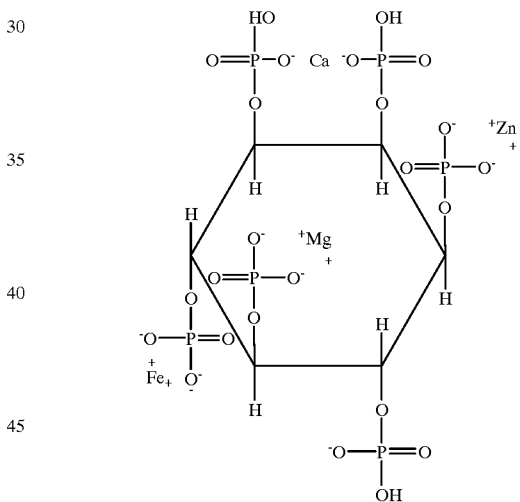

A feed additive such as the carboxylic acids and/or bioactive 1α-OH vitamin D compounds disclosed herein that causes the increased utilization of P from phytate should also increase utilization of these other elements as well. The present invention has established that a carboxylic acid, or a combination of a carboxylic acid with 1-α-OH vitamin D compounds, preferably 1,25 dihydroxycholecalciferol and 1-α-OH cholecalciferol, and/or phytase increases the utilization of not only P but also zinc, iron and manganese. Thus, because these three trace elements are always added in supplemental form to diets for swine, poultry and companion animals (as feed-grade ZnO or $ZnSO_4 \cdot H_2O$; $FeSO_4 \cdot H_2O$; MnO or $MnSO_4 \cdot H_2O$) use of a carboxylic acid, or a combination of a carboxylic acid with a bioactive 1-α-OH vitamin D compound and/or phytase would lower, or perhaps eliminate, the need for supplemental quantities of these mineral salts in a practical-type grain-oilseed meal diet.

By reducing or eliminating the inorganic P supplement and the supplement of trace mineral salts, the remaining diet would contain more usable energy. Thus, grain-oilseed meal diets generally contain about 3,200 kcal metabolizable energy per kilogram of diet, and mineral salts supply no metabolizable energy. Removal of the unneeded minerals and substitution with grain would therefore increase the usable energy in the diet.

Currently, phytase is being used in much of Europe and Asia to reduce P pollution. The use level, however, is 600 units per kilogram diet, but this level was selected because of cost of the enzyme and not because 600 units will maximize phytate utilization. In contrast it has been discovered via the present investigation that at least 1200 units/kg diet is required to maximize phytate utilization in chicks fed a corn-soybean meal diet (Table 1). However, use of a bioactive 1-α-OH vitamin D compound in accordance with the present invention would reduce the need to feed expensive levels of phytase. (Table 5)

Animal producers are forced to feed high P diets because of the phytate content of diets. This increases P in the excreta waste products (both feces and urine). Excess P from animal, as well as human waste, is generally spread on the soil, where a portion of it gets washed into ground water and then into ponds, streams, rivers, lakes and oceans. Too much P in water stimulates growth of algae, and algae take up considerable oxygen. This robs marine life of the oxygen they need to grow, reproduce and thrive.

In many parts of Europe and Asia, P pollution has become such a problem and concern that penalties in the form of stiff financial fines are imposed on livestock producers who spread too much P-laden manure on the soils. Because of this, much of Europe now uses a microbial phytase product (BASF), even though this product (which also hydrolyses phytate) is very expensive, in fact too expensive to be cost effective (at 600 units/kg diet) as a feed additive in the U.S. at the present time. Many U.S. soils are being described as "P saturated", thus resulting in a greater concentration of P in soil leachates. High-P water leachate in areas such as the Chesapeak Bay has been blamed for excessive algae growth and increased fish kills in bay waters (Ward, 1993). In Europe, the feed industry group FEFANA issued a position paper in 1991 entitled "Improvement of the Environment". They proposed that P in manure from livestock production should be reduced by 30% (Ward, 1993). The limits of P that can be applied to soils in Europe have been discussed by Schwarz (1994). Accordingly, it is estimated that use of a carboxylic acid, or a combination of a carboxylic acid with a 1-α-OH vitamin D compound that is active in increasing phosphorus utilization in accordance with the present invention, could cut the P content of animal waste products by up to 80%.

Initial work focused on use of 1,25 dihydroxycholecalciferol (1,25-$(OH)_2D_3$) in the absence or presence of 1200 units of microbial phytase (BASF), Edwards (1993) showed that 1,25-$(OH)_2D_3$ is effective in improving P utilization from phytate-bound P, and Biehl et al (1995) confirmed his results. Moreover, both studies showed that 1,25-$(OH)_2D_3$ works additively with microbial phytase in releasing P from dietary phytate complexes. It seems likely that 1,25-$(OH)_2D_3$ exerts is effects in two ways: (a) the 1,25 compound likely increases the activity of intestinal phytases or phosphatases that hydrolyze phytate (Pileggi et al, 1955; Maddaiah et al, 1964) and (b) the 1,25 compound is known to stimulate phosphate transport (Tanka and DeLuca, 1974), facilitating transport of P from GI tract to plasma and hence bone.

Under normal dietary circumstances, cholecalciferol (vitamin $D_3$) that is added to a diet gets absorbed from the GI tract and is transported via blood to the liver where the liver enzyme 25-hydroxylase acts on the compound to cause formation of 25-OH $D_3$. This compound is the normal blood metabolite of cholecalciferol. A small portion of 25-OH $D_3$ undergoes a further hydroxylation step in the kidney, at the 1-α position, causing synthesis of the calciotropic hormone 1,25-$(OH)_2D_3$. Because 1,25-$(OH)_2D_3$ is expensive to synthesize and because oral 25-OH $D_3$ is not the active form in phosphate absorption, it was proposed that 1-α-OH $D_3$ would be an effective compound for increasing phosphate utilization. It has been discovered that 1α-hydroxylated vitamin D compounds and particularly 1-α-OH $D_3$ will be absorbed from the GI tract and then be transported to the liver where 25-hydroxylase would act upon it to bring about synthesis of 1,25-dihydroxylated compounds and particularly 1,25-$(OH)_2D_3$. A portion of these compounds would then be transported back to the GI tract where they would activate intestinal phosphate absorption. The net effect would be an increased utilization of P (also Zn, Fe, Mn and Ca) from the phytate complex as well as from the inorganic P supplement itself.

In summary, the potential benefits of the present invention include (1) reduction in or possible elimination of the need for inorganic P supplements for animal (including fish) diets; (2) reduction in P pollution of the environment; (3) reduction or possible elimination of the need for supplemental Zn, Mn and Fe in animal diets; and (4) reduction of the quantity of phytase needed for maximal P utilization from feeds.

DETAILED DESCRIPTION OF THE PREFERRED EMBODIMENT

The present invention provides an animal feed containing carboxylic acids either as the sole active ingredient to accomplish the improved results disclosed herein, or in combination with a bioactive 1α-hydroxy vitamin D compound and/or the enzyme phytase. The use of these carboxylic acids, preferably citric acid, in animal feeds removes calcium from plant based phytate complexes thereby allowing the phytate to solubilize making the phosphorus contained in the phytate complexes bioavailable for animals. These carboxylic acids also increase utillization of the P from inorganic sources in the diet thus further reducing the need for supplemental inorganic phosphorus. This results in a feed composition having a severe reduction of, and possibly the complete elimination of, supplemental inorganic phosphorus as an ingredient.

The carboxylic acids useful as the active ingredient are di- and tri-carboxylic acids derived from hydrocarbons by replacing two (di-) or three (tri-) hydrogen atoms by the carboxyl group, —COOH. Examples of dicarboxylic acids include maleic acid, fumaric acid, succinic acid, malic acid, oxalic acid and tartaric acid. Examples of tricarboxylic acids include citric acid, isocitric acid, trans and cis aconitic acid, and homo citric acid. These acids may be used in all isomeric and/or stereochemical configurations. The preferred acid is citric acid, but it is believed any di- or tri-carboxylic acid may be used to achieve the advantages of the present invention.

The H atom of the carboxyl group of di- and tri-carboxylic acids is known to ionize in solution and thus exist in a monovalent ionic form such as citrate or oxalate. These ionic forms readily convert to corresponding salts with the result that di- and tri-carboxylic acids may thus be in the form of sodium, potassium, lithium, magnesium, calcium, or ammonium salts. These salts as well as the monovalent ions may be used in addition to the pure acid form without hindering the performance of the present invention.

Thus, in this specification and claims, the term "carboxylic acid" is intended to encompass not only the acid itself, but also the ionic and salt forms of the acid. Also, it should be noted that the carboxylic acid may be incorporated into an animal feed either in pure form or as a crude mixture with other ingredients, e.g. as a component of fermentation broth (obtained from the fermentation process used to produce such acids as citric acid or tartaric acid).

In order to accomplish the desired results of reducing and/or eliminating the addition of supplemental inorganic P to animal feeds, the animal's diet should contain from about 0.5% to about 10% carboxylic acid. Preferably, a diet containing about 2% to about 7% carboxylic acid should be employed. The preferred acid is citric acid. However, a combination of citrate and sodium citrate has also been found to be extremely effective.

As used in the description and in the claims, the term hydroxy-protecting group signifies any group commonly used for the temporary protection of hydroxy functions, such as for example, alkoxycarbonyl, acyl, alkylsilyl, and alkoxyalkyl groups, and a protected hydroxy group is a hydroxy function derivatized by such a protecting group. Alkoxycarbonyl protecting groups are groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, amlonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxyethyl, methoxyethoxymethyl, or tetrahydrofuranyl and tetrahydropyranyl. Preferred alkylsilyl protecting groups are trimethylsilyl, triethylsilyl, t-butyldimethylsilyl, and analogous alkylated silyl radicals.

The vitamin D compounds useful in the present treatment are 1α-hydroxylated vitamin D compounds, preferably 1α-hydroxycholecalciferol and 1α,25-dihydroxycholecalciferol. The vitamin D compounds of this type are characterized by the following general structure:

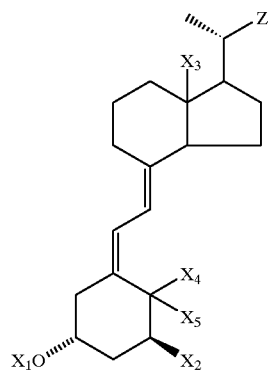

where $X_1$ may be hydrogen or a hydroxy-protecting group, $X_2$ may be hydroxy, or protected hydroxy, $X_3$ may be hydrogen or methyl, $X_4$ and $X_5$ each represent hydrogen or taken together $X_4$ and $X_5$ represent a methylene group, and where Z is selected from Y, —OY, —CH$_2$OY, —C≡CY and —CH═CHY, where the double bond may have the cis or trans stereochemical configuration, and where Y is selected from hydrogen, methyl, —CR$_5$O and a radical of the structure:

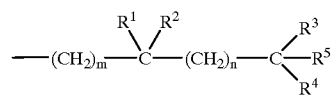

where m and n, independently, represent integers from 0 to 5, where $R^1$ is selected from hydrogen, hydroxy, protected-hydroxy, fluoro, trifluoromethyl, and $C_{1-5}$-alkyl, which may be straight chain or branched and, optionally, bear a hydroxy or protected-hydroxy substituent, and where each of $R^2$, $R^3$ and $R^4$, independently, is selected from hydrogen, fluoro, trifluoromethyl and $C_{1-5}$ alkyl, which may be straight-chain or branched, and optionally bear a hydroxy or protected-hydroxy substituent, and where $R^1$ and $R^2$, taken together, represent an oxo group, or an alkylidene group, ═CR$_2$R$_3$, or the group —(CH$_2$)$_p$—, where p is an integer from 2 to 5, and where $R^3$ and $R^4$, taken together, represent an oxo group, or the group —(CH$_2$)$_q$—, where q is an integer from 2 to 5, and where $R^5$ presents hydrogen, hydroxy, protected-hydroxy, or $C_{1-5}$ alkyl.

The above carboxylic acids and vitamin D compounds may be administered alone to animals in an edible carrier or in combination with other feed additive agents. The above carboxylic acids and vitamin D compounds or combinations thereof can be readily administered as a top dressing or by mixing them directly into animal feed or separately from the feed, by separate oral dosage, by injection or by transdermal means or in combination with other growth related edible compounds, the proportions of each of the compounds in the combination being dependent upon the particular problem being addressed and the degree of response desired, are generally effective to practice the present invention. In poultry, amounts in excess of about 10% carboxylic acids or of about 10 micrograms per day of 1α-hydroxylated vitamin D compounds, are generally unnecessary to achieve the desired results, may result in hypercalcemia, and may not be an economically sound practice. It should be understood that the specific dosage administered in any given case will be adjusted in accordance with the specific compounds being administered, the problem to be treated, the condition of the subject and the other relevant facts that may modify the activity of the effective ingredient or the response of the subject, as is well known by those skilled in the art. In general, either a single daily dose or divided daily dosages may be employed, as is well known in the art.

If administered separately from the animal feed, dosage forms of the various compounds can be prepared by combining them with non-toxic pharmaceutically acceptable edible carriers to make either immediate release or slow release formulations, as is well known in the art. Such edible carriers may be either solid or liquid such as, for example, corn starch, lactose, sucrose, soy flakes, peanut oil, olive oil, sesame oil and propylene glycol. If a solid carrier is used the dosage form of the compounds may be tablets, capsules, powders, troches or lozenges or top dressing as microdispersable forms. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

The present invention also relates to an animal feed composition and method of compounding an animal feed utilizing carboxylic acid or a combination of carboxylic acid and a 1α-hydroxylated vitamin D compound and/or the enzyme phytase to lower and/or eliminate the dietary requirement of phosphorus in the animal feed. The 1α-hydroxylated vitamin D compounds suitable for this use have been previously described herein. The amount of a phosphorus supplement (18.5% P) that may be incorporated with the feed may be reduced to 0% to about 0.9% on a dry weight basis. This is a significant reduction from the normal amount of phosphorus supplement incorporated in animal feed compositions of about 1.5% to about 2.5%. This beneficial reduction in phosphorus is a direct result of the incorporation of carboxylic acid or a combination of carboxylic acid and a 1α-hydroxylated vitamin D compound and/or the enzyme phytase in the animal feed.

The animal feed may be any protein-containing organic meal normally employed to meet the dietary requirements of animals. Many of such protein-containing meals are typically primarily composed of corn, soybean meal or a corn/soybean meal mix. For example, typical commercially available products fed to fowl include Egg Maker Complete, a poultry feed product of Land O'Lakes AG Services, as well as Country Game & Turkey Grower a product of Agwa, Inc. Both of these commercially available products are typical examples of animal feeds with which the present carboxylic acid or a combination of carboxylic acid and 1a-hydroxylated vitamin D compounds and/or the enzyme phytase may be incorporated to reduce or eliminate the amount of supplemental phosphorus, zinc, manganese and iron intake required in such compositions. Thus, any type of protein-containing organic meal may be utilized as the base mix to which the carboxylic acids, 1α-hydroxylated vitamin D compounds or phytase, and reduced supplemental phosphorus, zinc, manganese and iron amounts of the present invention may be incorporated.

The present invention is applicable to the diet of numerous animals, which herein is defined as including mammals, fowl and fish. In particular, the diet may be employed with commercially significant mammals such as pigs, cattle, sheep, goats, laboratory rodents (rats, mice, hamsters and gerbils), fur-bearing animals such as mink and fox, and zoo animals such as monkeys and apes, as well as domestic mammals such as cats and dogs. Typical commercially significant fowl include chickens, turkeys, ducks, geese, pheasants and quail. Commercially farmed fish such as trout would also benefit from the diet disclosed herein.

In a method of compounding feed for animals in accordance with the present invention, the carboxylic acid utilized is incorporated with the animal feed in an amount of from about 5 g/kg to about 100 g/kg feed on a dry weight basis. As noted previously, this amount is sufficient to provide about 0.5% to about 10% of the animal's diet. Also, the 1α-hydroxylated vitamin D compounds utilized is incorporated with the animal feed in an amount of from about 5 μg/kg to about 40 μg/kg feed on a dry weight basis. The feed mixture is then fed as a mash or is formed into desired discrete shapes for further processing and packaging. In general, these discrete shapes may be pellets, blocks or briquettes formed by known extrusion and/or compacting techniques. The particular processing technique utilized does not affect the performance of the carboxylic acid, the 1α-hydroxylated vitamin D compounds or the phytase in the animal feed mixture. The present invention is more specifically described by the following examples, which are meant to be illustrative only.

EXAMPLE 1

The object of this test was to determine if adding citrate/sodium citrate or oxalate/sodium oxalate to a P- & Ca-deficient diet improves P utilization.

DESCRIPTION

Young broiler chickens were fed a Phosphorus (P)-deficient corn-soybean meal diet that was designed to contain 23% protein, 0.62% Calcium (Ca), 25 μg/kg D3 and 0.42% Phosphorus (0.28% phytate P, 0.14% nonphytate P). The phytate P is considered essentially unavailable in this diet, and the diet is therefore severely deficient in "available" P (the NRC requirement for "available" P is 0.45%). Calcium is set at 0.62% (below the NRC requirement of 1.0%) so as to keep the Calcium "available" Phosphorus ratio at about 6:1 (the desired ratio is between 1:1 and 2:1).

GENERAL PROCEDURES

Housing, handling, and killing procedures were in accord with the policies of the University of Illinois Committee on Laboratory Animal Care. The chick bioassay involved male New Hampshire x Columbian chicks from the University of Illinois Poultry Farm. Chicks were housed in heated starter batteries with raised wire floors in an environmentally controlled building with 24-h constant overhead fluorescent lighting. During the first 7 d posthatching, chicks were fed a 23% CP, methionine-fortified corn-soybean meal diet that was adequate in Ca, P, and D3. After being deprived of feed overnight, chicks were weighed and wingbanded. After selecting birds of a narrow weight range, the chicks were randomly assigned to pens. Chicks were fed their assigned experimental diets on an ad libitum basis from day 8 to day 22 posthatching. Each of the six dietary treatments was fed to four replicate pens of four chicks during a 14-day assay feeding period.

At the end of each assay, chicks were killed by CO2 gas, and right tibiae from all chicks were quantitatively removed. Tibiae were pooled by replicate pen, and after removal of adhering tissue, they were dried for 24 h at 100° C. Dried bone samples were weighed and then dry ashed for 24 hours at 600° C. in a muffle furnace. Ash weight was expressed as a percentage of dry tibia weight and also as ash weight per tibia.

The Phosphorus deficient basal diet (94%) was fortified with graded doses of a citric acid (tricarboxylic acid)+ sodium citrate mixture (1:1) and one treatment diet consisted of a mixture of 0.50% oxalic acid (dicarboxylic acid) and 0.50% sodium oxalate. Cornstarch was varied to make all diets total to 100% (94% basal diet+6% added acids and/or cornstarch).

| Basal diet: | Ingredient | Percent |
| --- | --- | --- |
| | Corn | 45.35 |
| | SBM | 41.23 |
| | Soybean Oil | 5.00 |
| | Limestone | 1.32 |
| | Salt | 0.40 |
| | Farm Vitamin Mix | 0.20 |
| | Mineral Mix | 0.15 |
| | DL-Met | 0.20 |
| | Choline chloride | 0.10 |
| | Flavomycin | 0.05 |

TREATMENTS
1. Basal+6% cornstarch
2. Basal+5% cornstarch+0.5% Citrate+0.5% Na Citrate
3. Basal+4% cornstarch+1.0% Citrate+1.0% Na Citrate
4. Basal+2% cornstarch+2.0% Citrate+2.0% Na Citrate
5. Basal+0% cornstarch+3.0% Citrate+3.0% Na Citrate
6. Basal+5% cornstarch+0.5% Oxalate+0.5% Na Oxalate
Data were analyzed statistically by analysis of variance.
RESULTS

TABLE 1

| Organic Acid Addition | Level (%) | 14-d Weight Gain (g) | 14-d Feed Intake (g) | Gain:Feed (g/kg) | Tibia Ash (%) | Tibia Ash (Mg) |
| --- | --- | --- | --- | --- | --- | --- |
| 1. None | | 290$^c$ | 448$^{d,c}$ | 647$^a$ | 26.9$^c$ | 284$^a$ |
| 2. Citrate + Na Citrate | 0.5 + 0.5 | 289$^c$ | 441$^a$ | 655$^a$ | 27.9$^d$ | 305$^{d,c}$ |
| 3. Citrate + Na Citrate | 1.0 + 1.0 | 312$^b$ | 478$^{b,c}$ | 652$^c$ | 30.6$^c$ | 348$^c$ |
| 4. Citrate + Na Citrate | 2.0 + 2.0 | 330$^b$ | 502$^b$ | 657$^a$ | 35.6$^b$ | 436$^b$ |
| 5. Citrate + Na Citrate | 3.0 + 3.0 | 354$^a$ | 550$^a$ | 643$^a$ | 38.6$^a$ | 519$^a$ |
| 6. Oxalate + Na Oxalate | 0.5 + 0.5 | 276$^c$ | 473$^{c,d}$ | 584$^b$ | 31.4$^c$ | 329$^{c,d}$ |
| Pooled SEM | | 5.6 | 7.4 | 9.0 | 0.5 | 11 |

[1]Data are mean values of four pens of four chicks fed the diets from day 8 to day 22 posthatching; average initial weight was 100 g.
[a–c]Means in columns with different superscript letters are significantly ($p < 0.05$) different.

DISCUSSION OF RESULTS

Beginning at 1% citrate and 1% Na citrate, chicks gained faster when this combination was supplemented. With 3% citrate+3% Na citrate, the weight gain response was 22% greater than that of chicks fed the unfortified negative-control diet. The weight gain response occurred almost entirely as a result of increased voluntary feed intake, i.e. there was no improvement in efficiency of weight gain (gain:feed ratio). The oxalate mixture did not increase weight gain, but it did decrease feed efficiency.

The bone-ash response to citrate+Na citrate was linear ($p<0.01$) in response to increasing doses of the citrate ($p<0.01$). With 3% citrate+3% Na citrate in the diet, bone ash concentration was increased by 43%, and total bone ash (mg/tibia) was increased by 83%. The oxalate mixture (0.5% oxalic acid+0.5% Na oxalate) also increased ($p<0.05$) bone ash, and this suggests that any tri- or di-carboxylic organic acid will show efficacy in solubilizing phytate. Thus, maleic acid, fumaric acid, succinic acid, malic acid, oxalic acid, tartaric acid, isocitric acid, aconitic acid, homo citric acid and others would likely show phytate P-releasing efficacy.

EXAMPLE 2

Chick Efficacy Trials

A. Procedures:

The best measure of P (or Ca) activity in animals fed a P-deficient diet is total bone ash. In the present bioassay system, young chicks (8 d of age) are fed a corn-soybean meal diet containing 0.6% Ca and 0.43% total P, but an estimated 0.10% bioavailable P. The required levels of Ca and P for chicks of this age are 1.0% Ca and 0.45% available P (i.e., nonphytate P). Calcium is kept at 0.6% instead of 1.0% in our diet because excess Ca in the presence of a severe available P deficiency causes anorexia.

Generally speaking, three or four pens of three or four chicks per pen are placed on each dietary treatment. They are fed the experimental diets free choice for 12 d in wire-screened battery pens located in a environmentally controlled animal room with constant (fluorescent) lighting. At assay termination on d 20 posthatching, chicks are killed by cervical dislocation and the left tibia is quantitatively removed. Bones are stripped of adhering tissue, dried for 24 h at 100° C., weighed and then dry ashed for 24 h at 600° C. (muffle furnace). The portion remaining after ashing is entirely inorganic matter. The weight of ash (mineral matter) as a percent of dry bone weight is percent ash (mineral, and mostly Ca and P) in the bone. Percent ash multiplied by dry bone weight gives total bone ash in milligrams. Tibia ash reflects the degree of ash (or bone mineralization) in the entire skeleton. Our 20-d-old crossbred chicks (New Hampshire x Columbian) fed a diet adequate in Ca and P generally have percent bone ash values of 45%.

For assessment of Zn and Mn bioavailability, bone content of Zn and Mn are the established criteria, but growth responses are also used for assessment of Zn bioavailability (Wedekind et al, 1992; Halpin and Baker, 1986). For assessment of Zn or Mn bioavailability, the tibiae are dried at 100° C. for 24 h, weighed, and then dry ashed at 600° C. for another 24 h. The dried ash is then wet ashed with $HNO_3$ and $H_2O_2$. Zinc and manganese are then quantified using atomic absorption spectrophotometry (Wedekind et al, 1992). In research involving Zn, Mn or Fe (hemoglobin assay) bioavailability, the chicks are fed a pretest diet (0 to d-8 posthatching) that is deficient in Zn, Mn or Fe. This depletes stores of these trace elements. The experiments are then carried out in stainless-steel chick batteries equipped with stainless-steel feeders and waterers. Deionized water is available free choice. These steps are taken to avoid Zn, Mn or Fe contamination from the environment, equipment and drinking water.

B. Results:

The basal diet for this experiment was designed to be severely deficient in available P (most coming from phytate-bound P) but adequate to excess in vitamin $D_3$, and marginal in both Zn and Mn (i.e., no supplemental Zn or Mn in diet). Increases in bone ash would indicate enhanced GI absorption of P, and increases in bone Zn and Mn would indicate enhanced GI absorption of Zn and Mn (Chung and Baker, 1990; Wedekind et al, 1992; Halpin and Baker, 1986; Baker et al, 1986). As shown in Table 2, growth rate was increased (P<0.05) 17% by 0.10% P addition, 20% by 1200 U phytase addition, 15.5% by 1,25-$(OH)_2D_3$ addition, and 25% by the combination of phytase (1200 U) and 10.0 µg/kg 1,25-$(OH)_2D_3$. Bone ash, however, is the best measure of P bioavailability. Total bone ash (mg) was increased (P<0.01) 56% by 0.10% P addition (proving that P was severely deficient in the diet), 64% with 1200 U phytase, 60% by 1,25-$(OH)_2D_3$, and 98% by the combination of phytase and 1,25-$(OH)_2D_3$. Tibia Zn (µg) was increased (P<0.01) 55% by either 1200 U phytase or 10 µg/kg 1,25-$(OH)_2D_3$, but was increased 86% by the phytase-di-OH $D_3$ combination. Tibia Mn (µg) was increased (P<0.01) 63% by phytase, 85% by di-OH $D_3$ and 123% by the phytase-di-OH $D_3$ combination.

Data in Table 3 show results of a second efficacy trial. The basal diet for this trial was made adequate in Ca, and also was fortified with normal (safety factor) levels of Mn and Zn. It was thus singly deficient in available P. Bone ash was markedly depressed in chicks fed the P-deficient negative control diet. In fact, bone ash percent was about 5% lower (30.4% in Exp. 1, 25.5% in Exp. 2) in these chicks, a reflection of the high ratio of Ca to available P. Efficacy was again demonstrated for both phytase and 1,25-$(OH)_2D_3$. Moreover, the diet containing both phytase and 1,25-$(OH)_2D_3$ produced both ash values that were not far from those achieved with a P adequate diet (diet 5).

Data in Table 4 show results of a classic Zn efficacy trial. The basal diet was singly deficient in Zn (the NRC 1994 Zn requirement is 40 ppm) so that even with 10 ppm Zn addition, the diet was still Zn deficient. Marked efficacy was observed for both phytase and 1,25-$(OH)_2D_3$, and additivity was again evident for the combination.

Having shown conclusively that 1,25-$(OH)_2D_3$ is markedly efficacious in utilization of P, Zn and Mn, a trial was next conducted to test the efficacy of 1-α-OH $D_3$. These results are shown in Table 5. A linear (P<0.01) growth response occurred when 1-α-OH $D_3$ doses between 0 and 20 µg/kg were supplemented. Tibia ash likewise increased (P<0.01) markedly when 1-α-OH $D_3$ was added to the diet. Total tibia ash (mg) was 69% higher in chicks fed the diet with 20 µg/kg 1-α-OH $D_3$ than in those fed the unsupplemented basal diet. A dose of 40 µg/kg 1-α-OH $D_3$ was efficacious, and certainly nontoxic, but the 20 µg/kg dose maximized the response attributable to P release from phytate.

Data in Table 6 verify the synergism between the combination of microbial phytase and 1,25-$(OH)_2D_3$. Also, the results demonstrate that when phytase (600 vs. 1200 units) doses are compared in the presence of 10 µg/kg 1,25-$(OH)_2D_3$, 600 units of phytase are as effective as 1200 units in improving phytate-P utilization. This finding when compared to the data of Table 2 indicates that the phytase supplementation level required for maximum response can be cut in half if a supplemental bioactive 1-α-OH vitamin D compound is also included in the diet. In fact, only 300 units of phytase produced a marked response in the presence of 1,25-$(OH)_2D_3$.

Data in Table 7 show that synergism exists between 1-α-OH $D_3$ and phytase. Thus, 20 µg/kg 1-α-OH $D_3$ combined with 1200 units of phytase increased total bone ash by 107% over that observed for the basal unsupplemented corn-soybean meal diet. Supplemental 1-α-OH $D_3$ alone increased bone ash by 74%, and supplemental phytase alone increased bone ash by 65%.

TABLE 2

Phytase and 1,25-Dihydroxycholecalciferol Increase Growth Rate and Bone strength of Young Chicks Fed a Phosphorus-Deficient Diet (Exp. 1)[1]

| Diet[2] | Weight gain (g) | Gain feed (g/kg) | Avail. P intake (mg) | Tibia data[3] | | | | | | |
|---|---|---|---|---|---|---|---|---|---|---|
| | | | | Weight (mg) | Ash (%) | Ash (mg) | Zn (µg/g) | Zn (µg) | Mn (µ/g) | Mn (µg) |
| Phosphorus titration[4] | | | | | | | | | | |
| 0 | 193 | 644 | 300 | 667 | 30.4 | 203 | | | | |
| 0.05% P | 200 | 640 | 468 | 717 | 35.4 | 254 | | | | |
| 0.10% P | 226 | 657 | 688 | 827 | 38.3 | 317 | | | | |
| Phytase titration | | | | | | | | | | |
| 0 | 193 | 644 | 300 | 667 | 30.4 | 203 | 142 | 95 | 2.32 | 1.55 |
| 300µ phytase[5] | 202 | 647 | 312 | 729 | 33.9 | 247 | 145 | 105 | | |
| 600µ phytase | 206 | 661 | 312 | 735 | 35.8 | 263 | 159 | 117 | 2.66 | 1.96 |
| 900µ phytase | 224 | 664 | 338 | 805 | 38.2 | 308 | 171 | 137 | | |
| 1200µ phytase | 231 | 679 | 340 | 848. | 39.3 | 333 | 173 | 147 | 3.00 | 2.53 |
| Factorial | | | | | | | | | | |
| 1. 0 | 193 | 644 | 300 | 667 | 30.4 | 203 | 142 | 95 | 2.32 | 1.55 |
| 2. 1200 U phytase[5] | 231 | 679 | 340 | 848 | 39.3 | 333 | 173 | 147 | 3.00 | 2.53 |

TABLE 2-continued

Phytase and 1,25-Dihydroxycholecalciferol Increase Growth Rate and Bone strength of Young Chicks Fed a Phosphorus-Deficient Diet (Exp. 1)[1]

| Diet[2] | Weight gain (g) | Gain feed (g/kg) | Avail. P intake (mg) | Tibia data[3] | | | | | | |
|---|---|---|---|---|---|---|---|---|---|---|
| | | | | Weight (mg) | Ash (%) | Ash (mg) | Zn ($\mu$g/g) | Zn ($\mu$g) | Mn ($\mu$/g) | Mn ($\mu$g) |
| 3. 10 $\mu$g/kg DiOH-$D_3$[6] | 223 | 683 | 326 | 816 | 39.6 | 324 | 179 | 147 | 3.52 | 2.87 |
| 4. As 2 + 3 | 241 | 707 | 340 | 932 | 43.1 | 402 | 190 | 177 | 3.85 | 3.46 |
| Pooled SEM | 3.3 | 6.7 | | 14 | .5 | 7.0 | 4.1 | 4.4 | .10 | .08 |

Table 2 Footnotes
[1]Data represent means per chick of four replicate pens of four female chicks during the period 8 to 20-d posthatching; average initial weight was 82 g.
[2]The basal corn-sdybean meal diet (23% CP) contained 0.10% available P and 0.60% Ca. Neither Mn or Zn were provided as supplements to this basal diet. The diet was adequate to excess in vitamin $D_3$, containing 1000 IU of supplemental cholecalciferol per kg of diet (25 $\mu$g/kg).
[3]Dry weight basis.
[4]Graded doses of P from $KH_2PO_4$.
[5]Phytase obtained from BASF Corp., Parsippany, NJ 07054. One unit (U) of phytase is defined as the quantity of enzyme required to liberate 1 $\mu$mol of inorganic P per minute from 1.5 mmol/L sodium phytase at pH 5.5 and 37° C. Phytase was added from a premix (Natuphos ® 5,000 BASF) that contained 5,000 U of phytase activity per gram.
[6]Dihydroxycholecaiciferol (DiOH-$D_3$) obtained from Hoffman-LaRoche, Inc., Nutley, NJ. DiOH-$D_3$ was dissolved in propylene glycol to make a solution of 10 $\mu$g/ml. The desired volume of DiOH-$D_3$ solution for each diet involved was then dissolved in petroleum ether, which was then premixed with basal diet and subsequently added to the completed diet for mixing.

TABLE 3

Effects of Phytase and 1,25 Dihydroxycholecalciferol on Performance and Bone Characteristics of Chicks Fed Diets Deficient in Phosphorus and Adequate in Calcium (Exp. 2)[1]

| Diet | 12-d weight gain (g) | Gain feed (g/kg) | Avail. P intake (mg) | Tibia data[2] | | | | | | |
|---|---|---|---|---|---|---|---|---|---|---|
| | | | | Weight (mg) | Ash (%) | Ash (mg) | Zn ($\mu$g/g) | Zn ($\mu$g) | Mn ($\mu$/g) | Mn ($\mu$g) |
| 1. Basal (B)3 | 172 | 649 | 266 | 598 | 25.5 | 152 | 146 | 88 | 3.29 | 1.98 |
| 2. B + 1200$\mu$ phytase[4] | 218 | 678 | 322 | 780 | 37.5 | 292 | 219 | 171 | 4.82 | 3.76 |
| 3. B + 10 $\mu$g/kg diOH-$D_3$[5] | 201 | 686 | 293 | 698 | 36.1 | 253 | 199 | 139 | 5.29 | 3.69 |
| 4. As 2 + 3 | 219 | 702 | 311 | 847 | 42.5 | 360 | 216 | 183 | 5.86 | 4.96 |
| 5. B + .45% P[6] | 244 | 688 | 1952 | 959 | 45.3 | 435 | 189 | 181 | 3.54 | 3.39 |
| Pooled SEM | 4.4 | 7.1 | | 22 | .45 | 9.5 | 5 | 6 | .13 | .12 |

[1]Data represent mean values per chick of four replicates (pens) of three chicks during the period 8 to 20-d posthatching; average initial weight was 83 g.
[2]Intact left tibia (dry basis).
[3]The basal corn-soybean meal diet (23% CP) contained .10% available P and 1.0% Ca. Both Mn and Zn were provided as supplements to this basal diet (50 mg/kg of each) such that the basal diet was singly deficient in available P.
[4]See footnote 5 of Table 1.
[5]See footnote 6 of Table 1.
[6]Provided from $KH_2PO_4$.

TABLE 4

Efficacy of Phytase and 1,25 Di-OH-$D_3$ in Chicks Fed a Zn-Deficient Diet (Exp. 3)[1]

| Diet[2] | 12 days gain (g) | Tibia Zn ($\mu$g/g) | Tibia Zn ($\mu$g) |
|---|---|---|---|
| 1. Basal diet | 169 | 44.7 | 34.2 |
| 2. As 1 + 1200 U phytase | 209 | 62.2 | 54.9 |
| 3. As 1 + 10 $\mu$g/kg Di-OH-$D_3$ | 201 | 60.3 | 53.1 |
| 4. As 2 + 3 | 241 | 88.4 | 88.7 |
| 5. As 1 + 5 ppm Zn (ZnSO$_4$.7H$_2$O) | 210 | 61.5 | 54.2 |
| 6. As 2 + 10 ppm Zn (ZnSO$_4$.7H$_2$O) | 236 | 73.7 | 71.1 |
| Pooled SEM | 08 | | 2.7 |

[1]Data are means of four pens, each containing four male chicks weighing 84.5 g at day 8 posthatching; 12-d feeding period in stainless-steel batteries with chicks receiving deionized water. During the 8-d pretest period, chicks were fed a low Zn soybean meal diet.
[2]Soy concentrate-dextrose diet containing 13 ppm Zn.

TABLE 5

Dietary Addition of 1-α-hydroxycholecalciferol Increases Phytate-Phosphorus Utilization (Exp. 4)[1]

| Dietary Level of 1-α-OH-D$_3$ ($\mu$/kg) | 12-d weight gain[3] (g) | Gain feed[3] (g/kg) | Tibia Data[3] Weight (mg) | Ash (%) | Ash (mg) |
|---|---|---|---|---|---|
| 0 | 228[b] | 645[b] | 724[c] | 33.0[b] | 238[c] |
| 10 | 255[a] | 676[a] | 917[b] | 38.9[a] | 356[b] |
| 20 | 266[a] | 681[a] | 992[a] | 40.5[a] | 402[a] |
| 40 | 255[a] | 677[a] | 878[b] | 41.1[a] | 361[b] |
| Pooled SEM | 3.6 | 6.5 | 21 | .75 | 7.6 |

[1]Means of three pens of four chicks during the period 8 to 20 days posthatching.
[2]Added to a corn-soybean meal diet (23% CP) containing adequate vitamin D-3, 0.60% Ca and 0.43% P (0.10% estimated available P).
[3]Means within columns with unlike superscript letters are significantly (P < 0.5) different.

TABLE 6

Performance and Bone Ash of Chicks Fed 1,25-Dihydroxycholecalciferol in the Absence or Presence of Three Levels of Microbial Phytase (Exp. 5)[1]

| Dietary addition[2] | Weight gain[3] (g) | Food intake (g) | Tibia data[3] Weight (mg) | Ash (%) | Ash (mg) |
|---|---|---|---|---|---|
| 1. None | 203[c] | 314[c] | 672[c] | 32.9[4] | 238[d] |
| 2. 10 $\mu$g/kg di-OH-D$_3$ | 234[b] | 338[b] | 825[b] | 42.2[c] | 348[c] |
| 3. As 2 + 300 U phytase | 244[a] | 349[a,b] | 881[a,b] | 42.5[b,c] | 375[b] |
| 4. As 2 + 600 U phytase | 251[a] | 361[a] | 903[a] | 43.9[a,b] | 396[a,b] |
| 5. As 2 + 1200 U phytase | 252[a] | 356[a] | 886[a] | 44.7[a] | 396[a,b] |
| Pooled SEM | 3.6 | 4.6 | 20 | 0.5 | 9.0 |

[1]Data are means for four pens of four female chicks that were fed the experimental diets during the period 8 to 20 d posthatching; average initial weight was 93 g. Means in columns with different superscripts letters are significanfly different (P < 0.05).
[2]The basal diet (Table 1) contained, by analysis, 0.43% P (0.10% estimated available P), 0.63% Ca and 23% crude protein.
[3]Dry weight basis.

TABLE 7

Evaluation of 1-α-Hydroxycholecalciferol With and Without Phytase on Phosphorus Utlization[1]

| Dietary addition | Weight gain g | Food intake g | Tibia data Weight mg | Ash g/100 g | Ash mg |
|---|---|---|---|---|---|
| 1. None | 195[c] | 306[b] | 634[c] | 29.1[c] | 185[c] |
| 2. 0.10 g P/100 g (KH$_2$PO$_4$) | 239[a,b] | 355[a] | 801[b] | 38.7[b] | 310[b] |
| 3. 1200 U phytase | 245[a,b] | 356[a] | 795[b] | 38.5[b] | 306[b] |
| 4. 20 $\mu$g/kg 1-α-OH-D$_3$ | 235[b] | 343[a] | 787[b] | 40.9[a] | 321[b] |
| 5. As 3 + 4 | 253[a] | 363[a] | 897[a] | 42.7[a] | 384[a] |
| Pooled SEM | 5.5 | 6.6 | 18 | 0.7 | 11 |

[1]Data are means of three pens of four female chicks that are fed the experimental diets during the period 8 to 20 d posthatching; average initial weight was 88 g. Means in columns with different superscript letters are significantly different (P < 0.05).
[2]The basal corn-soybean meal diet contained, by analysis, 0.43 g P/100 g (0.10 g/100 g estimated nonphytate P), 0.63 g Ca/100 g and 23.9 g CP/100 g.
[3]Dry-weight basis.

We claim:

1. A method of enhancing utilization of phosphorus present in feed for fowl, comprising the step of: feeding to fowl a feed additive containing a tricarboxylic acid or a salt of said tricarboxylic acid in an amount of from about 2% to about 10% by weight of feed on a dry weight basis for making phosphorus in feed bioavailable to said fowl.

2. The method of claim 1 wherein said tricarboxylic acid is selected from the group consisting of citric acid, isocitric acid, trans aconitic acid, cis aconitic acid and homo citric acid.

3. The method of claim 1 wherein said salt is selected from the group consisting of sodium, potassium, lithium, magnesium, calcium and ammonium salts.

4. The method of claim 1 wherein said additive contains sodium citrate.

5. The method of claim 1 wherein the phosphorus made available is from phytate complexes in said feed.

6. The method of claim 1 wherein the phosphorus made available is from inorganic sources in said feed.

7. The method of claim 1 further including the step of incorporating a 1α-hydroxylated vitamin D compound with said additive in an amount which provides from about 5 $\mu$g/kg to about 40 $\mu$g/kg of feed, said 1α-hydroxylated vitamin D compound is characterized by the following general structure:

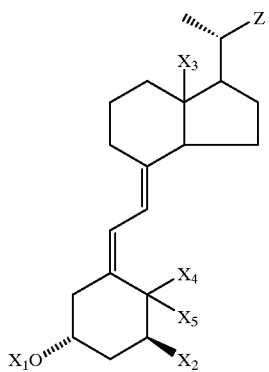

where $X_1$ may be hydrogen or a hydroxy-protecting group, $X_2$ may be hydroxy, or protected hydroxy, $X_3$ may be hydrogen or methyl, $X_4$ and $X_5$ each represent hydrogen or taken together $X_4$ and $X_5$ represent a methylene group, and where Z is selected from Y, —OY, —CH$_2$OY, —C≡CY and —CH═CHY, where the double bond may have the cis or trans stereochemical configuration, and where Y is selected from hydrogen, methyl, —CR$_5$O and a radical of the structure:

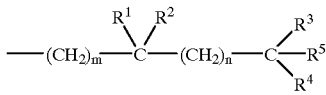

where m and n, independently, represent integers from 0 to 5, where $R^1$ is selected from hydrogen, hydroxy, protected-hydroxy, fluoro, trifluoromethyl, and C$_{1-5}$-alkyl, which may be straight chain or branched and, optionally, bear a hydroxy or protected-hydroxy substituent, and where each of $R^2$, $R^3$ and $R^4$, independently, is selected from hydrogen, fluoro, trifluoromethyl and C$_{1-5}$ alkyl, which may be straight-chain or branched, and optionally bear a hydroxy or protected-hydroxy substituent, and where $R^1$ and $R^2$, taken together, represent an oxo group, or an alkylidene group, ═CR$_2$R$_3$ or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected-hydroxy, or C$_{1-5}$ alkyl.

8. The method of claim 1 further including the step of incorporating phytase with said additive in an amount of from about 300 units to about 1,200 units per kilogram of feed.

9. The method of claim 7 wherein the vitamin D compound is 1α-hydroxyvitamin D$_3$.

10. The method of claim 7 wherein the vitamin D compound is 1α,25-dihydroxyvitamin D$_3$.

11. The method of claim 1 wherein said fowl is selected from the group consisting of chickens, turkeys, ducks, geese, pheasant and quail.

12. The method of claim 1 wherein the step of feeding said additive comprises adding said additive as a top dressing on feed.

13. The method of claim 1 wherein the step of feeding said additive comprises mixing said additive directly into the feed so that said additive is fed simultaneously with the feed.

14. The method of claim 1 wherein the step of feeding said additive comprises administering said additive to fowl separately from the feed.

15. A method of minimizing dietary requirements of phosphorus in fowl comprising the step of:

feeding to fowl a feed additive containing a tricarboxylic acid or a salt of said tricarboxylic acid in an amount of from about 2% to about 10% by weight of feed on a dry weight basis for making phosphorus in feed bioavailable to said fowl.

16. The method of claim 15 wherein said tricarboxylic acid is selected from the group consisting of citric acid, isocitric acid, trans aconitic acid, cis aconitic acid and homo citric acid.

17. The method of claim 15 wherein said salt is selected from the group consisting of sodium, potassium, lithium, magnesium, calcium and ammonium salts.

18. The method of claim 15 wherein said additive contains sodium citrate.

19. The method of claim 15 wherein the phosphorus made available is from phytate complexes in said feed.

20. The method of claim 15 wherein the phosphorus made available is from inorganic sources in said feed.

21. The method of claim 15 further including the step of incorporating a 1α-hydroxylated vitamin D compound with said additive in an amount which provides from about 5 μg/kg to about 40 μg/kg of feed, said 1α-hydroxylated vitamin D compound is characterized by the following general formula:

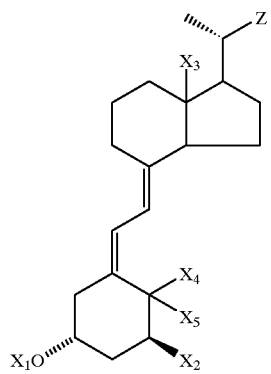

where X$_1$ may be hydrogen or a hydroxy-protecting group, X$_2$ may be hydroxy, or protected hydroxy, X$_3$ may be hydrogen or methyl, X$_4$ and X$_5$ each represent hydrogen or taken together X$_4$ and X$_5$ represent a methylene group, and where Z is selected from Y, —OY, —CH$_2$OY, —C≡CY and —CH═CHY, where the double bond may have the cis or trans stereochemical configuration, and where Y is selected from hydrogen, methyl, —CR$_5$O and a radical of the structure:

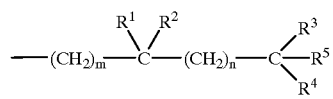

where m and n, independently, represent integers from 0 to 5, where R$^1$ is selected from hydrogen, hydroxy, protected-hydroxy, fluoro, trifluoromethyl, and C$_{1-5}$-alkyl, which may be straight chain or branched and, optionally, bear a hydroxy or protected-hydroxy substituent, and where each of R$^2$, R$^3$ and R$^4$, independently, is selected from hydrogen, fluoro, trifluoromethyl and C$_{1-5}$ alkyl, which may be straight-chain or branched, and optionally bear a hydroxy or protected-hydroxy substituent, and where R$^1$ and R$^2$, taken together, represent an oxo group, or an alkylidene group, ═CR$_2$R$_3$ or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected-hydroxy, or C$_{1-5}$ alkyl.

22. The method of claim 21 wherein the vitamin D compound is 1α-hydroxyvitamin D$_3$.

23. The method of claim 21 wherein the vitamin D compound is 1α,25-dihydroxyvitamin D$_3$.

24. The method of claim 15 further including the step of incorporating phytase with said additive in an amount of from about 300 units to about 1,200 units per kilogram of feed.

25. The method of claim 15 wherein said fowl is selected from the group consisting of chickens, turkeys, ducks, geese, pheasant and quail.

26. The method of claim 15 wherein the step of feeding said additive comprises adding said additive as a top dressing on feed.

27. The method of claim 15 wherein the step of feeding said additive comprises mixing said additive directly into the feed so that said additive is fed simultaneously with the feed.

28. The method of claim 15 wherein the step of feeding said additive comprises administering said additive to fowl separately from the feed.

29. A method of enhancing inorganic phosphorus utilization from inorganic phosphorus sources in feed for fowl, comprising the step of:

feeding to fowl a feed additive containing a tricarboxylic acid or a salt of said tricarboxylic acid in an amount of from about 2% to about 10% by weight of feed on a dry weight basis for making inorganic phosphorus contained in feed bioavailable to said fowl.

30. The method of claim 29 wherein said tricarboxylic acid is selected from the group consisting of citric acid, isocitric acid, trans aconitic acid, cis aconitic acid and homo citric acid.

31. The method of claim 29 wherein said salt is selected from the group consisting of sodium, potassium, lithium, magnesium, calcium and ammonium salts.

32. The method of claim 29 wherein said additive contains sodium citrate.

33. The method of claim 29 wherein the inorganic phosphorus made available is from an inorganic phosphorus supplement added to said feed.

34. The method of claim 29 further including the step of incorporating a 1α-hydroxylated vitamin D compound with said additive in an amount which provides from about 5 μg/kg to about 40 μg/kg of feed said 1α-hydroxylated vitamin D compound is characterized by the following general formula:

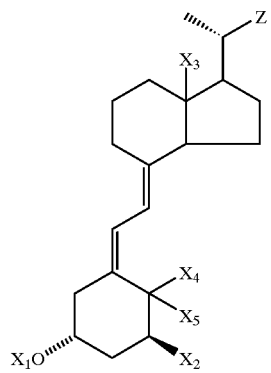

where $X_1$ may be hydrogen or a hydroxy-protecting group, $X_2$ may be hydroxy, or protected hydroxy, $X_3$ may be hydrogen or methyl, $X_4$ and $X_5$ each represent hydrogen or taken together $X_4$ and $X_5$ represent a methylene group, and where Z is selected from Y, —OY, —CH$_2$OY, —C≡—CY and —CH═CHY, where the double bond may have the cis or trans stereochemical configuration, and where Y is selected from hydrolen, methyl, —CR$_5$O and a radical of the structure:

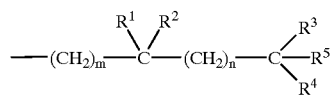

where m and n, independently, represent integers from 0 to 5, where $R^1$ is selected from hydrogen, hydroxy, protected-hydroxy, fluoro, trifluoromethyl, and $C_{1-5}$-alkyl, which may be straight chain or branched and, optionally, bear a hydroxy or protected-hydroxy substituent, and where each of $R^2$, $R^3$ and $R^4$, independently, is selected from hydrogen, fluoro, trifluoromethyl and $C_{1-5}$ alkyl, which may be straight-chain or branched, and optionally bear a hydroxy or protected-hydroxy substituent, and where $R^1$ and $R^2$, taken together, represent an oxo group, or an alkylidene group, =CR$_2$R$_3$ or the group —(CH$_2$)$_p$—, where p is an integer from 2 to 5, and where $R^3$ and $R^4$, taken together, represent an oxo group, or the group —(CH$_2$)$_q$—, where q is an integer from 2 to 5, and where $R^5$ represents hydrogen, hydroxy, protected-hydroxy, or $C_{1-5}$ alkyl.

35. The method of claim 34 wherein the vitamin D compound is 1α-hydroxyvitamin D$_3$.

36. The method of claim 34 wherein the vitamin D compound is 1α,25-dihydroxyvitamin D$_3$.

37. The method of claim 29 further including the step of incorporating phytase with said additive, in an amount of from about 300 units to about 1,200 units per kilogram of feed.

38. The method of claim 29 wherein said fowl is selected from the group consisting of chickens, turkeys, ducks, geese, pheasant and quail.

39. The method of claim 29 wherein the step of feeding said additive comprises adding said additive as a top dressing on feed.

40. The method of claim 29 wherein the step of feeding said additive comprises mixing said additive directly into the feed so that said additive is fed simultaneously with the feed.

41. The method of claim 29 wherein the step of feeding said additive comprises administering said additive to fowl separately from the feed.

42. A method of enhancing organic phosphorus utilization from organic phosphorus sources in feed for fowl, comprising the step of:

feeding to fowl a feed additive containing a tricarboxylic acid or a salt of said tricarboxylic acid in an amount of from about 2% to about 10% of feed on a dry weight basis for making organic phosphorus contained in feed bioavailable to said fowl.

43. The method of claim 42 wherein said tricarboxylic acid is selected from the group consisting of citric acid, isocitric acid, trans aconitic acid, cis aconitic acid and homo citric acid.

44. The method of claim 42 wherein said salt is selected from the group consisting of sodium, potassium, lithium, magnesium, calcium and ammonium salts.

45. The method of claim 42 wherein said additive contains sodium citrate.

46. The method of claim 42 wherein the organic phosphorus made available is from phytate complexes in said feed.

47. The method of claim 42 further including the step of incorporating a 1α-hydroxylated vitamin D compound with said additive in an amount which provides from about 5 μg/kg to about 40 μg/kg of feed, said 1α-hydroxylated vitamin D compound is characterized by the following general formula:

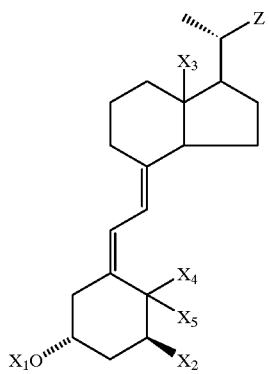

where $X_1$ may be hydrogen or a hydroxy-protecting group, $X_2$ may be hydroxy, or protected hydroxy, $X_3$ may be hydrogen or methyl, $X_4$ and $X_5$ each represent hydrogen or taken together $X_4$ and $X_5$ represent a methylene group, and where Z is selected from Y, —OY, —CH$_2$OY, —C≡CY and —CH=CHY, where the double bond may have the cis or trans stereochemical configuration, and where Y is selected from hydrogen, methyl, —CR$_5$O and a radical of the structure:

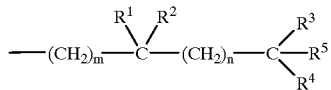

where m and n, independently, represent integers from 0 to 5, where $R^1$ is selected from hydrogen, hydroxy, protected-hydroxy, fluoro, trifluoromethyl, and $C_{1-5}$-alkyl, which may be straight chain or branched and, optionally, bear a hydroxy or protected-hydroxy substituent, and where each of $R^2$, $R^3$ and $R^4$, independently, is selected from hydrogen, fluoro, trifluoromethyl and $C_{1-5}$ alkyl, which may be straight-chain or branched, and optionally bear a hydroxy or protected-hydroxy substituent, and where $R^1$ and $R^2$, taken together, represent an oxo group, or an alkylidene group, =CR$_2$R$_3$ or the group —(CH$_2$)$_p$—, where p is an integer from 2 to 5, and where $R^3$ and $R^4$, taken together, represent an oxo group, or the group —(CH$_2$)$_q$—, where q is an integer from 2 to 5, and where $R^5$ represents hydrogen, hydroxy, protected-hydroxy, or $C_{1-5}$ alkyl.

48. The method of claim 47 wherein the vitamin D compound is 1α-hydroxyvitamin D$_3$.

49. The method of claim 47 wherein the vitamin D compound is 1α,25-dihydroxyvitamin D$_3$.

50. The method of claim 42 further including the step of incorporating phytase with said additive in an amount of from about 300 units to about 1,200 units per kilogram of feed.

51. The method of claim 42 wherein said fowl is selected from the group consisting of chickens, turkeys, ducks, geese, pheasant and quail.

52. The method of claim 42 wherein the step of feeding said additive comprises adding said additive as a top dressing on feed.

53. The method of claim 42 wherein the step of feeding said additive comprises mixing said additive directly into the feed so that said additive is fed simultaneously with the feed.

54. The method of claim 47 wherein the step of feeding said additive comprises administering said additive to fowl separately from the feed.

55. A method of minimizing dietary requirements of inorganic phosphorus in fowl comprising the step of:

feeding to fowl a feed additive containing a citrate in an amount of from about 2% to about 10% by weight of feed on a dry weight basis for making inorganic phosphorus contained in feed bioavailable to said fowl.

56. The method of claim 55 wherein the inorganic phosphorus made available is from an inorganic phosphorus supplement added to said feed.

57. The method of claim 55 further including the step of incorporating a 1α-hydroxylated vitamin D compound with said additive in an amount which provides from about 5 μg/kg to about 40 μg/kg of feed, said 1α-hydroxylated vitamin D compound is characterized by the following general formula:

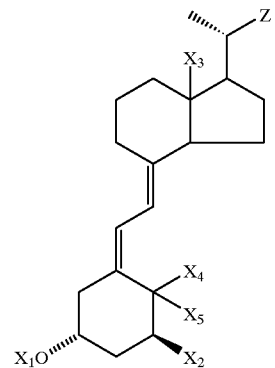

where $X_1$ may be hydrogen or a hydroxy-protecting group, $X_2$ may be hydroxy, or protected hydroxy, $X_3$ may be hydrogen or methyl, $X_4$ and $X_5$ each represent hydrogen or taken together $X_4$ and $X_5$ represent a methylene group, and where Z is selected from Y, —OY, —CH$_2$OY, —C≡CY and —CH=CHY, where the double bond may have the cis or trans stereochemical configuration, and where Y is selected from hydrogen, methyl —CR$_5$O and a radical of the structure:

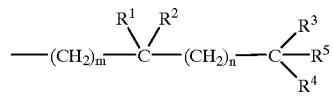

where m and n, independently, represent integers from 0 to 5, where $R^1$ is selected from hydrogen, hydroxy, protected-hydroxy, fluoro, trifluoromethyl, and $C_{1-5}$-alkyl, which may be straight chain or branched and, optionally, bear a hydroxy or protected-hydroxy substituent, and where each of $R^2$, $R^3$ and $R^4$, independently is selected from hydrogen, fluoro, trifluoromethyl and $C_{1-5}$ alkyl, which may be straight-chain or branched, and optionally bear a hydroxy or protected-hydroxy substituent, and where $R^1$ and $R^2$, taken together, represent an oxo group, or an alkylidene group, =CR$_2$R$_3$ or the group —(CH$_2$)$_p$—, where p is an integer from 2 to 5, and where $R^3$ and $R^4$, taken together, represent an oxo group, or the group —(CH$_2$)$_q$—, where q is an integer from 2 to 5, and where $R^5$ represents hydrogen, hydroxy, protected-hydroxy, or $C_{1-5}$ alkyl.

58. The method of claim 57 wherein the vitamin D compound is 1α-hydroxyvitamin D$_3$.

59. The method of claim 57 wherein the vitamin D compound is 1α,25-dihydroxyvitamin D$_3$.

60. The method of claim 55 further including the step of incorporating phytase with said additive in an amount of from about 300 units to about 1,200 units per kilogram of feed.

61. The method of claim 55 wherein said fowl is selected from the group consisting of chickens, turkeys, ducks, geese, pheasant and quail.

62. The method of claim 55 wherein the step of feeding said additive comprises adding said additive as a top dressing on feed.

63. The method of claim 55 wherein the step of feeding said additive comprises mixing said additive directly into the feed so that said additive is fed simultaneously with the feed.

64. The method of claim 55 wherein the step of feeding said additive comprises administering said additive to a fowl separately from the feed.

* * * * *

UNITED STATES PATENT AND TRADEMARK OFFICE
CERTIFICATE OF CORRECTION

PATENT NO. : 6,022,555
DATED : February 8, 2000
INVENTOR(S) : Hector F. DeLuca et al.

It is certified that error appears in the above-identified patent and that said Letters Patent is hereby corrected as shown below:

<u>Column 19, claim 34,</u>
Line 50, delete "-C≡-CY" and substitute therefor -- C≡CY --

Signed and Sealed this

Fifth Day of February, 2002

Attest:

JAMES E. ROGAN
*Attesting Officer*    *Director of the United States Patent and Trademark Office*